(12) United States Patent
Beevers

(10) Patent No.: US 7,331,348 B1
(45) Date of Patent: Feb. 19, 2008

(54) INFANT CPAP NASAL CANNULA SEAL

(76) Inventor: Timothy R. Beevers, 14670 Baker Creek Rd., McMinnville, OR (US) 97128

( * ) Notice: Subject to any disclaimer, the term of this patent is extended or adjusted under 35 U.S.C. 154(b) by 883 days.

(21) Appl. No.: 10/667,728

(22) Filed: Sep. 22, 2003

(51) Int. Cl.
*A61M 15/08* (2006.01)

(52) U.S. Cl. .............. 128/207.18; 128/DIG. 26; 128/200.26; 128/204.12

(58) Field of Classification Search ............ 128/200.24, 128/207.18, 912, DIG. 26, 911, 200.26, 207.17, 128/204.12, 206.11, 206.28; 604/94, 180, 604/174; 606/204.45; 602/41, 54, 903
See application file for complete search history.

(56) References Cited

U.S. PATENT DOCUMENTS

| | | | | |
|---|---|---|---|---|
| 2,245,658 A * | 6/1941 | Erickson | ................ | 128/206.28 |
| 3,430,300 A * | 3/1969 | Doan | ................ | 24/304 |
| 4,490,141 A * | 12/1984 | Lacko et al. | ................ | 604/180 |
| 4,534,342 A * | 8/1985 | Pexa | ................ | 602/74 |
| 4,774,946 A | 10/1988 | Ackerman et al. | ..... | 128/207.18 |
| 4,777,963 A * | 10/1988 | McKenna | ................ | 600/537 |
| 4,823,789 A * | 4/1989 | Beisang, III | ........... | 128/207.18 |
| 4,919,128 A | 4/1990 | Kopala et al. | ......... | 128/207.18 |
| 5,042,478 A | 8/1991 | Kopala et al. | ......... | 128/207.18 |
| 5,269,296 A | 12/1993 | Landis | ................ | 128/207.18 |
| 5,271,391 A | 12/1993 | Graves | ................ | 128/207.18 |
| 5,383,891 A * | 1/1995 | Walker | ................ | 606/196 |
| 5,477,852 A | 12/1995 | Landis et al. | ......... | 128/207.18 |
| 5,533,506 A | 7/1996 | Wood | ................ | 128/207.18 |
| 5,687,715 A | 11/1997 | Landis et al. | ......... | 128/207.18 |
| 5,735,272 A * | 4/1998 | Dillon et al. | ......... | 128/207.18 |
| 6,328,038 B1 | 12/2001 | Kessler et al. | ......... | 128/207.18 |
| 6,478,026 B1 | 11/2002 | Wood | ................ | 128/207.18 |
| 6,561,192 B2 | 5/2003 | Palmer | ................ | 128/207.17 |
| 6,595,215 B2 | 7/2003 | Wood | ................ | 128/207.18 |
| 6,966,318 B1 * | 11/2005 | Tsuug et al. | ........... | 128/206.11 |
| 2003/0116163 A1 | 6/2003 | Wood | ................ | 128/207.18 |

\* cited by examiner

*Primary Examiner*—Justine R. Yu
*Assistant Examiner*—Shumaya Ali
(74) *Attorney, Agent, or Firm*—Timothy E. Siegel

(57) ABSTRACT

A nasal CPAP cannula seal that includes a strip of flexible material, between about 3 to 10 cm in width and between about 5 to 15 cm in length. The strip defines a pair of substantially round nostril apertures, each aperture having a diameter of between 2 mm and 4.5 mm and being spaced apart by from 1.5 mm to 3 mm. Also, the strip further defines a set of cuts extending outwardly from each nostril aperture.

8 Claims, 5 Drawing Sheets

INFANT CPAP NASAL CANNULA SEAL

BACKGROUND OF THE INVENTION

Continuous positive airway pressure (CPAP) is becoming an increasingly common way of supporting ventilation in prematurely born infants who cannot breathe without intervention. Although CPAP may be done with intubation, this invention deals only with nasal CPAP.

A problem is presented, however, in the retention and sealing of the CPAP cannula (FIG. 1) to the delicate nostrils of a premature infant. Unfortunately, a problem that may be encountered in the contact between the cannula and the delicate skin of an infant. A spot where the cannula exerts too much pressure against the skin can cause a disruption in blood flow and necrosis may begin within 10 to 20 minutes of seal application. Currently, nurses fashion CPAP seals by cutting them out of wound dressing material made by hydrocolloid laminated to a 25 micrometer thick sheet of polyurethane. The requisite process of sterilization causes wound dressing to be opaque. Accordingly, when using a seal made of wound dressing, the attending health care professionals are unable to see if damage is being done to the skin by the pressure of the cannula without at least partially removing the seal. Another instance in which an opaque seal makes it more difficult to perform a vital inspection, is in checking for an accumulation of mucous in the nostril. Such an accumulation can plug the nostril if allowed to continue accumulating, endangering the infant's life. Health care professionals check for this hazard, typically with the use of a pen light.

Another problem that is encountered in the use of CPAP seals cut from wound dressing is the challenge to medical personnel to create a seal that accurately fits the infant nose and successfully accommodates the cannula. The ideal nostril aperture size is on the order of a few millimeters. It is a challenge, even for a highly dexterous professional, to correctly form apertures of this size through the use of a pair of scissors. In addition some medical professionals make the mistake of cutting out the seal so that it is sized according to the infant nose, rather than to the cannula that will be used. While some medical professionals use a hole punch to make the holes, it is difficult to line the hole punch correctly in order to match the hole spacing with the cannula prong spacing. Also, the hole punches readily available are not sized to match the cannula prongs, making it difficult for the professional to insert the prongs either before or after placing the seal on the patient. If the apertures do not fit the cannula properly, the seal may leave a path for air leakage, or may bunch up inside the nostril, causing discomfort.

Another issue is the time that it takes to form a CPAP seal. When a newborn infant is in trouble, every second counts. Time spent cutting out a CPAP seal could delay necessary treatment for an infant. Also, even if a supply of CPAP seals are cut out in advance, a typical hospital wing has no way to hermetically enclose the CPAP seals. So the ability to store the seals is limited to a few weeks at most. Moreover, when it is time to use a seal that has been already cut out of wound dressage, the fact that the seal itself is coincident in two dimensions with the releasable liner of the wound dressing causes a difficulty in prying the releasable liner away from the dressing as there is no excess liner available to be grasped separately from the wound dressing.

SUMMARY OF THE INVENTION

In a first separate aspect, the present invention is a nasal CPAP cannula seal that includes a strip of flexible material, between about 3 to 10 cm in width and between about 5 to 15 cm in length. The strip defines a pair of substantially round nostril apertures, each the aperture having a diameter of between 2 mm and 4.5 mm and being spaced apart by from 1.5 mm to 3 mm. Also, the strip further defines a set of cuts extending outwardly from each nostril aperture.

In a second separate aspect, the present invention is a nasal CPAP cannula seal. The seal is made of a strip of flexible material defining a nose-covering region that includes two nostril apertures. The strip of flexible material also defines adherence wings, adapted to adhere to a patient's cheeks and inwardly extending cuts between the nose-covering region and the adherence wings that facilitate the folding of nose covering-region relative to the adherence wings.

In a third separate aspect, the present invention is a nasal CPAP cannula seal that is made of a strip of flexible material defining a nose covering-region that includes two nostril apertures. Additionally, the material defines a pair of wings, adapted to adhere to an infant's cheeks. Also, the strip of flexible material is at least semi-transparent.

In a further separate aspect, the present invention is a nasal CPAP cannula seal assembly that includes a nasal CPAP cannula seal, contained within the substantially sanitary package. The CPAP cannula seal is a strip of flexible material defining a nose covering-region that includes two nostril apertures and a pair of wings adapted to adhere to an infant's cheeks. In addition, a liner is releasably adhered to the nasal CPAP cannula seal for easy handling, and a substantially sanitary package contains the nasal CPAP cannula seal adhered to the liner.

In a fifth separate aspect, the present invention is a nasal CPAP cannula seal assembly that includes a nasal CPAP cannula seal, which includes a strip of flexible material including a nose covering-region that defines two nostril apertures and a pair of wings, adapted to adhere to an infant's cheeks. Additionally, a liner is releasably adhered to the nasal CPAP cannula seal and extends outwardly from the nasal CPAP cannula seal, to provide a user with an area to grasp the liner when peeling the nasal CPAP cannula seal off of the liner.

In a sixth separate aspect, the present invention is a method of doing business, comprising producing and selling nasal CPAP seals in a plurality of differing sizes.

The foregoing and other objectives, features and advantages of the invention will be more readily understood upon consideration of the following detailed description of the preferred embodiment(s), taken in conjunction with the accompanying drawings.

DETAILED DESCRIPTION OF THE PREFERRED EMBODIMENT(S)

Figure 1:
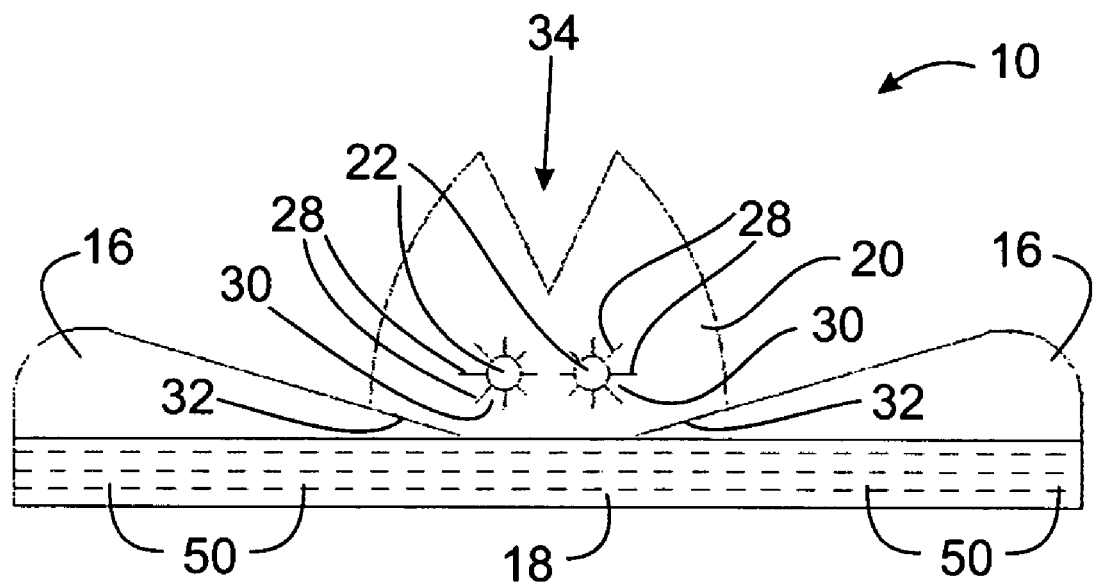
FIG. 1 is a top view of an infant nasal CPAP cannula seal according to the present invention.
Figure 2:
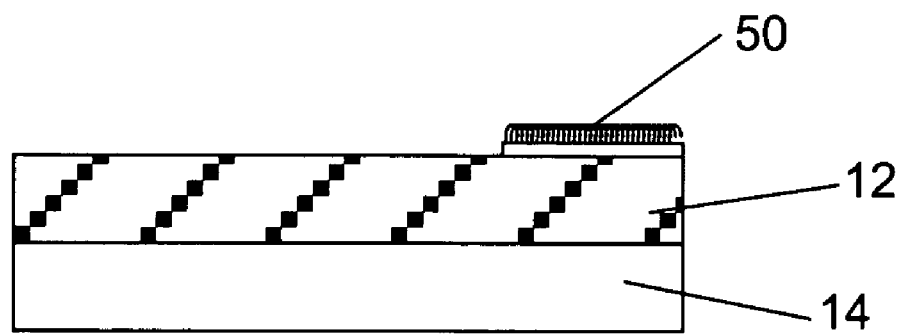
FIG. 2 is a cross-sectional view of the infant nasal CPAP cannula seal of FIG. 1, taken along line 2-2 of FIG. 1.

One embodiment of the present invention is a nasal CPAP seal 10 (FIG. 1). Referring to FIG. 2, seal 10 is made principally of a 25 micrometer thick strip of flexible polyurethane 12 having a hydrocolloid 14 (FIG. 2) laminated to it. Unlike CPAP seals that are cut out of wound dressing, seal 10 is semi-transparent. Wound dressing, because it is placed directly on an open wound, must be sterilized and because of its composition the only practical way of doing this is by bombarding it with gamma rays, which causes it to become opaque. Seal 10, however, is not intended for use in treating open wounds, but rather to be placed on intact skin and mucous membrane. Although the manufacturing process is sanitary, there is no need to sterilize the seals 10, allowing the production of a translucent, semi-transparent seal 10, which permits inspection of the underlying skin and mucous membrane. As noted in the Background section this inspection is extremely important in the prevention of skin necrosis due to an imperfectly applied seal and in the prevention of nasal passageway closure, due to mucous build-up, which is a potentially life threatening condition.

Figure 4A:
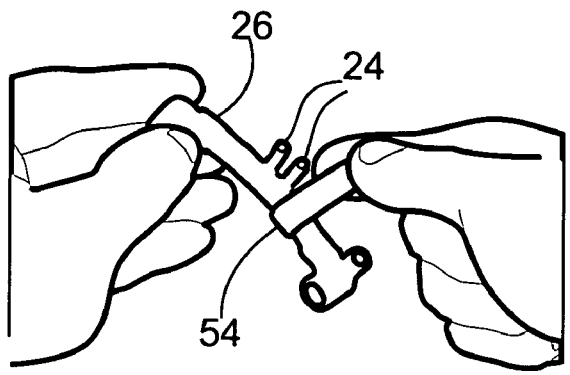
FIG. 4A is an illustration of placing a strip of loop material about a cannula in a method of using a CPAP cannula seal according to the present invention.
Figure 4B:
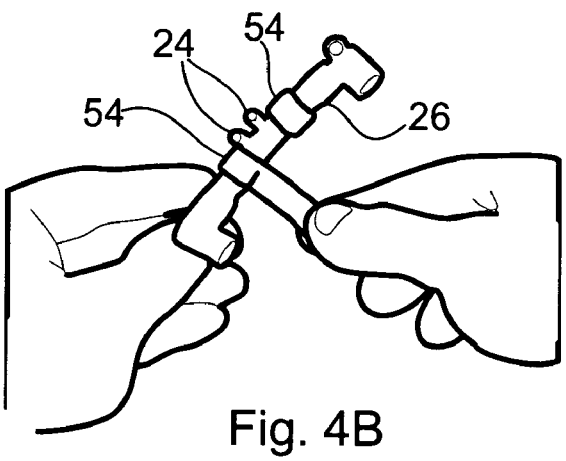
FIG. 4B is an illustration of placing an additional loop material about a cannula in a method of using a CPAP cannula seal according to the present invention.
Figure 4C:
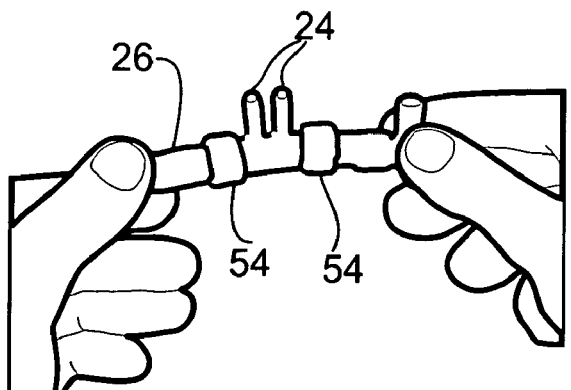
FIG. 4C is an illustration of a CPAP cannula seal having strips of loop material applied to, which represents a stage in a method of using a CPAP cannula seal according to the present invention.

Seal 10, which is between 10 mm and 15 mm long and between 3 mm and 10 mm wide, includes a pair of adherence wings 16, for gently fixing the seal 10 onto the cheeks of an infant patient and a lip covering region 18 for adherence to the upper lip. Toward the center of seal 10, a nose-covering region 20 defines a pair of apertures 22, which are between 2 mm and 4.5 mm in major axis length and are spaced apart by from 1.5 mm to 3 mm, and are adapted to accommodate a pair of terminal air channels 24 (FIGS. 4A-4C) of the CPAP cannula 26 (FIGS. 4A-4C). Although these apertures are shown as being round, as an alternative preferred embodiment they are D-shaped. Significantly, a set of radially outwardly extending cuts or stellations 28 emanate from each aperture 22. Not only do stellations 28 permit apertures 22 to accommodate any one of a few different cannula makes, as the cannula is inserted through aperture 22, a set of tabs 30 defined by the stellations 28 are pushed inwardly so that they extend into the infant's nostrils, contacting and providing gentle support to the delicate intranasal mucous membrane. Only very small stellations 28 emanate from the septum side of the apertures 22, to avoid weakening the thin strip of material between the apertures 22.

The nose-covering region 20 is defined, in part by a pair of cuts 32, which facilitate region 20 in being folded upwardly relative to the lip adherence region 18 and wings 16. Some embodiments do not include cuts 32, as the wound dressing material is quite flexible and compressible.

A v-shaped cleft 34 is defined by region 20 and helps region 20 fold in about the infant nose. In addition, a strip of hook material 50 is present on the lower part of lip covering region 18 and wings 16. Material 50 is used to attach seal 10 to the cannula 26, which is fitted with a pair of loop material strips 54 (FIGS. 4A-4C).

In addition material 50 imparts structural rigidity to seal 10, which is of value in the handling of seal 10.

A set of differently sized nasal CPAP seals of this make will be sold to accommodate various sizes of CPAP cannulas. It is anticipated that medical personnel will keep a range of seals on hand and pick an appropriate sized seal when needed.

Figure 3A:
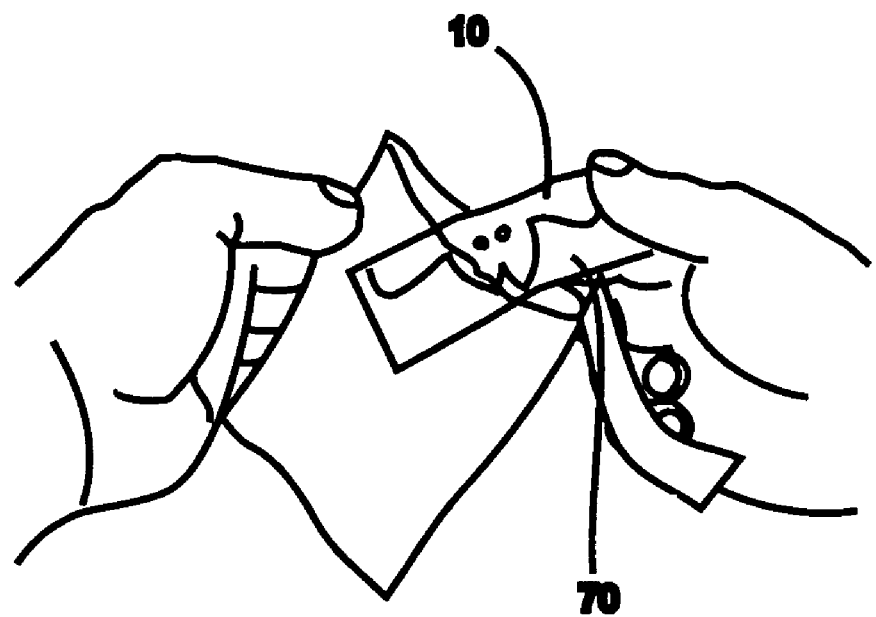
FIG. 3A is an illustration of opening an antiseptic container in a method of using a CPAP cannula seal according to the present invention.
Figure 3B:
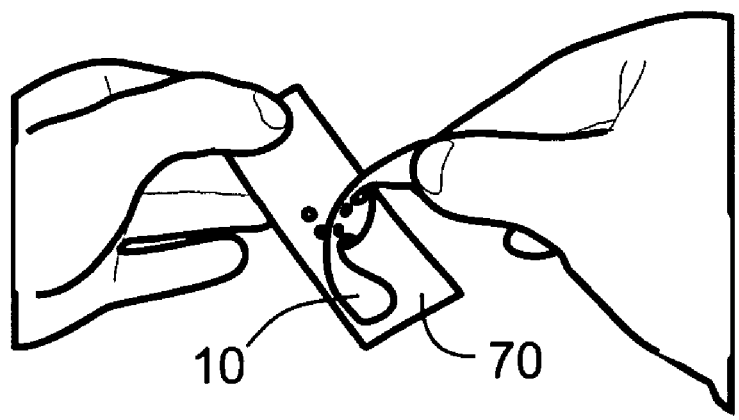
FIG. 3B is an illustration of peeling a cannula seal from its releasable liner in a method of using a CPAP cannula seal according to the present invention.
Figure 3C:
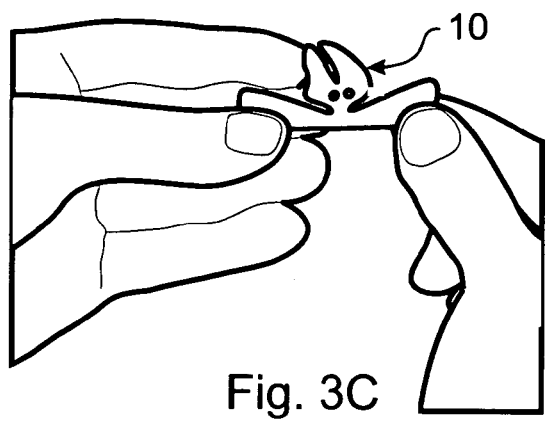
FIG. 3C is an illustration of carrying a cannula seal to an infant's face in a method of using a CPAP cannula seal according to the present invention.
Figure 3D:
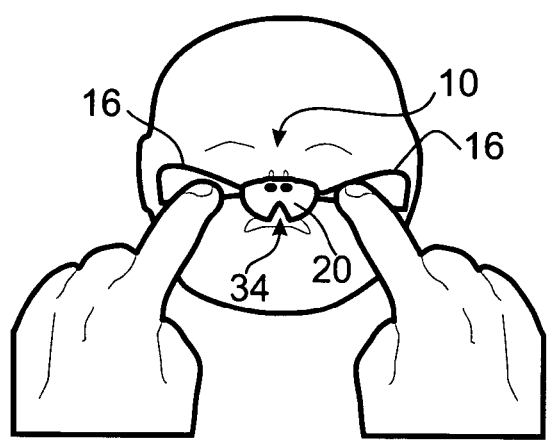
FIG. 3D is an illustration of placing a cannula seal of an infant's face in a method of using a CPAP cannula seal according to the present invention.
Figure 3E:
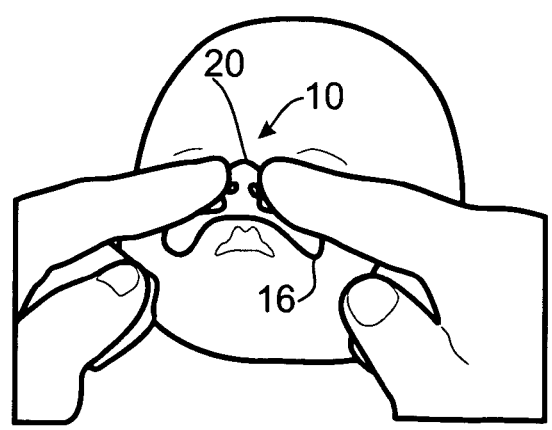
FIG. 3E is an illustration of placing a cannula seal over an infant's nose in a method of using the CPAP cannula seal according to the present invention.

Referring to FIGS. 3A-3E, a seal 10 is used by first removing it from a releasable liner 70 (FIG. 3B). It should be noted that liner 70 is not the same size and shape as seal 10, as it would be if seal and liner were simultaneously cut from the same piece of wound dressing, as is the current practice. As liner 70 extends outwardly beyond the limits of seal 10, it is easier for a user to first grasp liner 70 and then pry seal 10 free of it. In a neo-natal care unit setting where every second can make a difference to the health of the infant, this ease of use could well be a life saving feature in some instances. Next (FIG. 3C) seal 10 is supported in transport to the infant's face, so that adhering portions do not adhere to each other. Then, wings 16 are pressed into the infant patients cheeks (FIG. 3D). Finally nose-covering region 20 is folded upwardly to cover the infant nose, nostril apertures 22 are lined up with the nostrils (FIG. 3E) and region 20 is folded over the infant nose thereby closing cleft 34. Finally, terminal air channels 24 are fitted into nostril apertures 22 and loop material 54 (FIG. 4C) is mated to hook material 50 to keep cannula 26 supported and in place.

Figure 5A:
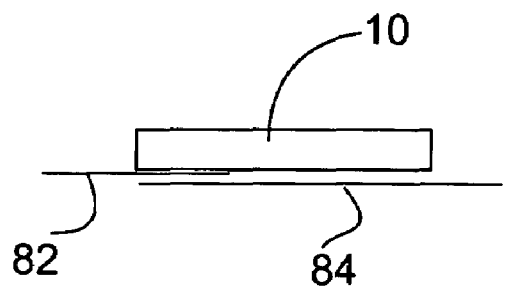
FIG. 5A is an illustration of an alternative CPAP cannula seal assembly according to the present invention, in which the releasable liner assembly includes a first releasable liner, and a second releasable liner overlaps said first releasable liner.
Figure 5B:
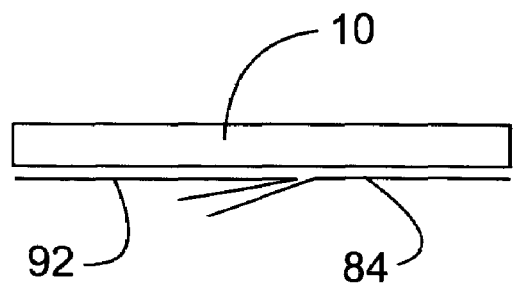
FIG. 5B is an illustration of an alternative CPAP cannula seal assembly according to the present invention, in which the releasable liner assembly includes a releasable liner and a tab.
Figure 5C:
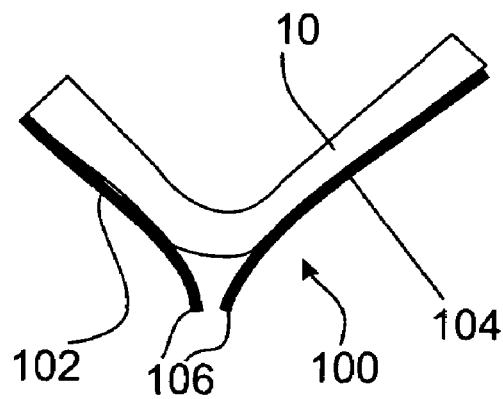
FIG. 5C is an illustration of an alternative CPAP cannula seal assembly according to the present invention, in which the releasable liner assembly includes a releasable liner that is cut into parts.

Referring to FIG. 5A, in an alternative preferred embodiment, a release liner assembly 80 is made up of two a first release liner 82, having a portion that is folded upwardly to provide a free area 86 and a second release liner 84, which overlaps liner 82, thereby providing a second free area 88 that a user may grasp in removing the second liner from the seal 10. FIG. 5B shows yet another release liner assembly 90 in which a tab 92 is interposed between release inner 84 and seal 10. In use tab 92 is grasped by a user and used to peel the release liner 84 away from seal 10. FIG. 5C shows a still further release liner assembly 100 having a first release 102 and a second release liner 104. When assembly 100 is bent and bowed outwardly, liners 102 and 104 partially separate from seal 10 to form a pair of free areas 106.

The terms and expressions that have been employed in the foregoing specification are used as terms of description and not of limitation. There is no intention, in the use of such terms and expressions, of excluding equivalents of the features shown and described or portions thereof, it being recognized that the scope of the invention is defined and limited only by the claims which follow.

The invention claimed is:

1. A nasal CPAP cannula seal, comprising:
   (a) a strip of flexible material, between about 3 to 10 cm in width and between about 5 to 15 cm in length; and
   (b) wherein said strip defines a pair of nostril apertures, each said aperture having a major axis length of between 2 mm and 4.5 mm, said apertures being spaced apart by from 1.5 mm to 3 mm; and
   (c) wherein said strip further defines a set of cuts extending outwardly from each said nostril aperture.

2. The nasal CPAP cannula seal of claim 1 wherein for each said nostril aperture, said cuts extending away from said nostril aperture do not include any cuts extending toward the other said nostril aperture.

3. The nasal CPAP cannula seal of claim 1 wherein said flexible material is made of a hydrocolloid laminated to a flexible polymer.

4. The nasal CPAP cannula seal of claim 3 wherein said flexible polymer is polyurethane.

5. A nasal CPAP cannula seal, comprising:
   (a) a strip of flexible material defining a nose-covering region that is sized and shaped to cover all of an infant nose and includes two nostril apertures sized and spaced apart so as to align with human infant nostrils;
   (b) said strip of flexible material also defining adherence wings, adapted to adhere to a patient's cheeks;
   (c) said strip of flexible material further defining a pair of inwardly extending cuts between said nose-covering region and said pair of wings that facilitate the folding of said nose-covering region relative to said pair of wings, and wherein in an unfolded state, said nose covering region and is positioned below abuts each of said pair of wings at said cuts.

6. The nasal CPAP cannula seal of claim 5 wherein for each said nostril aperture, said cuts extending away from said nostril aperture do not include any cuts extending toward the other said nostril aperture.

7. The nasal CPAP cannula seal of claim 5 wherein said flexible material is made of a hydrocolloid laminated to a flexible polymer.

8. The nasal CPAP cannula seal of claim 7 wherein said flexible polymer is polyurethane.

* * * * *